United States Patent [19]
MacFarlane et al.

[11] Patent Number: 5,307,210
[45] Date of Patent: Apr. 26, 1994

[54] BEAM ALIGNMENT DEVICE AND METHOD

[75] Inventors: Duncan L. MacFarlane, Dallas; Dale M. Byrne, Arlington, both of Tex.

[73] Assignee: Board of Regents, The University of Texas System, Austin, Tex.

[21] Appl. No.: 518,456

[22] Filed: May 3, 1990

[51] Int. Cl.$^5$ .............................................. G02B 5/10
[52] U.S. Cl. ................................... 359/859; 359/857; 359/858
[58] Field of Search ............... 359/857, 858, 859, 861, 359/862, 863, 864, 867, 868, 869

[56] References Cited

U.S. PATENT DOCUMENTS

| | | |
|---|---|---|
| 3,694,095 | 9/1972 | Louthan . |
| 3,887,263 | 6/1975 | Thompson, III . |
| 3,950,079 | 4/1976 | Rambauske . |
| 4,209,253 | 6/1980 | Hughes . |
| 4,367,017 | 1/1983 | Jimbou et al. . |
| 4,692,024 | 9/1987 | Bloss ................................ 359/858 |

FOREIGN PATENT DOCUMENTS 1365375  9/1974  United Kingdom .

*Primary Examiner*—Bruce Y. Arnold
*Assistant Examiner*—Hung Xuan Dang
*Attorney, Agent, or Firm*—Arnold, White & Durkee

[57] ABSTRACT

We describe a device for aligning optical beams that uses either an elliptically curved or a parabolically curved mirror arranged in the reflected beam path between a rotatable mirror, which is placed at the focus of the curved mirror, and the desired target. With the elliptical mirror, the device provides variable angle, fixed position of incidence of the reflected beam upon a target placed at the second focus of the ellipse. With the parabolic mirror, the device provides variable position, fixed angle of incidence of the reflected beam upon a target. Combinations of these devices may be used to solve a variety of beam steering and/or beam alignment problems. These devices are particularly useful for experiments and applications involving ultrashort optical pulses since the time of flight through either of these devices is a constant independent of the angle of incidence and the position of incidence.

10 Claims, 5 Drawing Sheets

BEAM ALIGNMENT DEVICE AND METHOD

BACKGROUND OF THE INVENTION

The invention relates to a device and a method for aligning optical beams. In particular, this invention relates to a general field of aligning optical beams for characterizing, testing, evaluating and applying linear and nonlinear optical materials and devices, electronic materials and devices, and mechanical materials and devices. Beam alignment is achieved using a device having either an elliptically curved or a parabolically curved mirror arranged in a reflected beam path between a rotatable mirror and the desired target. Combinations of both elliptical and parabolic mirrors may be used to solve a variety of beam steering and/or beam alignment problems.

Optical beams are typically steered by reflecting light from one or more moveable mirrors. Mirrors are moved or rotated with respect to the longitudinal axis of the optical beam path to produce a reflected or steered beam. The reflected beam is placed on a target material in accordance with the angle of rotation of the rotatable mirror. The rotatable mirror, often called a steering mirror, is typically the sole means for steering the reflected beam upon the target material. However, the steering mirror can be combined with a second mirror to direct the reflected beam onto the target material, wherein the second mirror is disposed within the reflected beam path and between the steering mirror and the target material. The second mirror, like the steering mirror, can be curved and can rotate independently or simultaneously with the steering mirror to optimally direct the reflected beam.

Merely reflecting optical beams by using a combination of rotatable mirrors and secondary mirrors does not provide adequate results in specific applications. Often it is desirable to place the reflected beam at a fixed position and vary, with a high degree of precision, the angle of incidence upon the target material. For ultrashort pulse non-linear optics experiments, for example, one must conserve momentum (phase matching) in addition to precisely controlling the temporal and spatial overlap of two or more beams upon the target material. Momentum is conserved by placing the various beams at the same position upon the target but at varying angles of incidence. Accordingly, a real need exists for an improved steering device and method which is also suitable for non-linear applications which can place an ultrashort optical beam at a precise point on a target but at varying angles of incidence.

In addition to being able to vary the angle of incidence upon a fixed target location, it is also highly desirable to direct a reflected beam at varying locations, but at a fixed angle of incidence. The reflected beam could be steered to arrive at different positions upon the target material while maintaining the same angle of incidence at each location. Like the variable angle, fixed position application, conventional steering techniques show difficulty in placing beams at variable positions upon a target while maintaining at fixed angle of incidence. In order to place reflected ultrashort beams evenly across a target, a real need exists for an improved steering device and method suitable for material and device characterization applications which can place an ultrashort optical beam at various points on a target while maintaining a fixed angle of incidence.

SUMMARY OF THE INVENTION

Accordingly, the present invention overcomes the prior art by providing an improved beam steering device and method, wherein a reflected optical beam can be placed upon a target at either a variable angle, fixed position, or a variable position, fixed angle. The improved device used for changing the angle of incidence of the beam upon the target while maintaining a constant or fixed position upon the target is accomplished using a rotatable mirror and an elliptical mirror placed within the reflected beam path and between the rotatable mirror and the target material. Similarly, the improved device used for changing the position of incidence of the beam upon the target while maintaining a constant angle of incidence is accomplished using a rotatable mirror and a parabolic mirror placed within the reflected beam path and between the rotatable mirror and target material. Either arrangement will provide selective control over the direction and placement of the reflected beam. These parameters may be varied continuously and smoothly with these devices. Furthermore, the two separate arrangements can be used in a variety of combinations as basic building blocks for any beam alignment task.

The improved device for aligning optical beams of the present invention provides not only a high degree of precision in directing the reflected beam upon the target, but also provides a constant travel time of the reflected beam from the rotatable mirror to the target material regardless of the rotatable mirror angle of rotation. Thus, for ultrafast optical beams having ultrashort pulsewidths, each beam in a plurality of beams will arrive at the target location at the same time independent of the rotatable mirror angle of rotation. Provided the mirrors have high quality smooth surfaces, reflected beams can be placed and can simultaneously arrive upon the target with a high degree of precision.

In a preferred embodiment, the improved device for aligning optical beams of the present invention comprises an elliptical mirror having a hole for receiving the optical beams, a rotatable mirror aligned with the beams for reflecting the beams upon the elliptical mirror, and a target for receiving the reflected beams at a fixed position substantially independent of the angle of rotation of the rotatable mirror. The rotatable mirror is configured at the first focal point of the ellipse. The target for receiving the reflected beams is situated at the second focal point of the ellipse. Moreover, the rotatable mirror can be either flat or curved depending upon the surface structure of the elliptical mirror. The rotatable mirror is preferably flat if the elliptical mirror is an ellipsoid. The rotatable mirror may also be a phase conjugate mirror in order to correct for phase front distortion. Alternatively, a small, collimated rotatable light source, such as a semiconductor diode laser, may replace the rotatable mirror.

In another preferred embodiment, an improved device for aligning optical beams of the present invention, comprises a parabolic mirror having a hole for receiving the optical beams, a rotatable mirror aligned with the optical beams for reflecting the beams upon the parabolic mirror, and a target for receiving the reflected beams at a fixed angle of incidence substantially independent of the angle of rotation of the rotatable mirror. The rotatable mirror is configured at the first focal point of the parabola. The target for receiving the reflected beams is situated within the path of travel of the reflected beam. Moreover, the rotatable mirror can be either curved or flat depending upon the surface characteristics of the parabolic mirror. A flat rotatable mirror is preferably used if the parabolic mirror is a paraboloid. The rotatable mirror may also be a phase conjugate mirror in order to correct for phase front distortion. Alternatively, a small, collimated rotatable light source, such as a semiconductor diode laser, may replace the rotatable mirror.

In still another preferred embodiment, an improved method for aligning optical beams of the present invention comprises combining at least two geometric mirrors in a cascaded configuration, passing the optical beams through a hole in a first geometric mirror onto a first rotatable mirror of the cascaded configuration. The optical beams are then reflected from the first rotatable mirror onto the first geometric mirror where they are then reflected through holes in geometric mirrors arranged subsequent to the first geometric mirror. Upon traveling through the holes of each subsequent geometric mirror, the reflected beams are then reflected back upon the respective geometric mirror and eventually onto a target by a rotatable mirror contained within each geometric mirror. The geometric mirrors can be elliptical or parabolic mirrors.

In still another preferred embodiment, an improved method for aligning optical beams of the present invention comprises combining at least two geometric mirrors, passing the optical beams through a hole in a first geometric mirror, reflecting the optical beams onto the first geometric mirror, receiving the reflected beams onto a target and onto a second geometric mirror, and transmitting the reflected beam through a hole in the second geometric mirror and upon a fixed detector. The reflected beam striking the target can either pass through or be reflected by the target material. Upon further reflection of the reflected beam from the target, the further reflected beam is received upon the second geometric mirror and then transmitted through a hole in the second geometric mirror and upon a fixed detector. However, if the reflected beam passes through the target material, then it is received upon the second geometric mirror arranged behind the target. The first and second geometric mirrors of either the transmissive or reflective target embodiments may be either elliptical or parabolic mirrors.

The present invention therefore provides an improved device and method for aligning optical beams which enjoys the advantages of directing beams via a rotatable mirror, while at the same time targeting the reflected beam at a fixed location with a variable angle of incidence or at a fixed angle of incidence with a variable point of incidence. Each application of the improved alignment device of the present invention can be cascaded or arranged in tandem as building blocks to provide a high degree of flexibility for any beam alignment task. These and other advantages of the present invention will be further appreciated from the drawings and the detailed description provided below.

DESCRIPTION OF THE PREFERRED EMBODIMENTS

Figure 1:
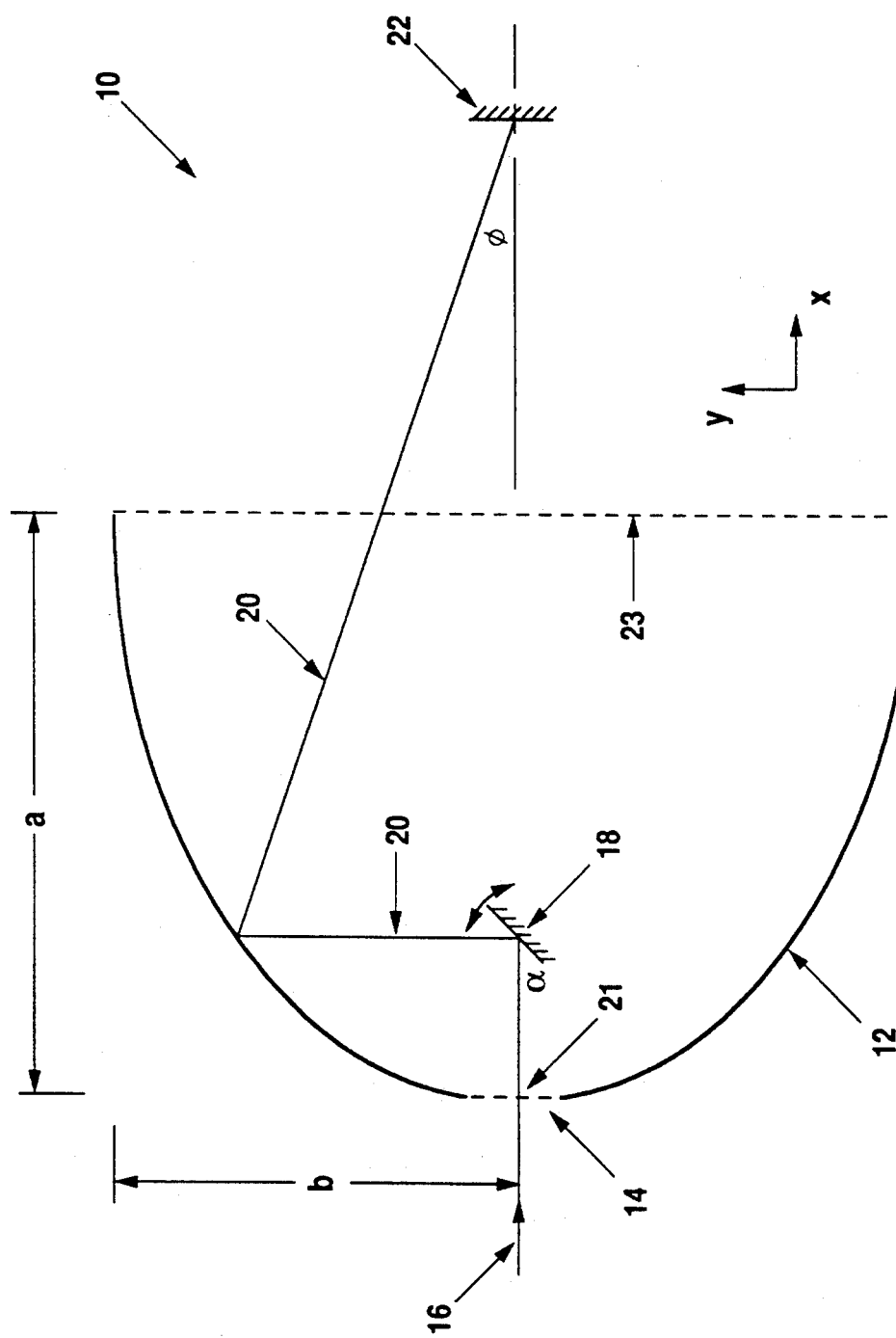
FIG. 1 is a cross-sectional view of a variable angle, fixed position beam alignment device of the present invention.

Referring to the drawings, FIG. 1 is a cross-sectional view of a variable angle, fixed position beam alignment device 10 of the present invention. Variable angle, fixed position device 10 comprises elliptical mirror 12 having hole 14 through which optical beam 16 is transmitted along the major axis of the ellipse. Optical beam 16 includes any narrow cross sectional stream of light particles, or photons, of any wavelength or wavelengths originated from either a laser or an incoherent source. In addition, the principles of this invention are suitable to direct charged and uncharged particle beams. Whatever type of beams are chosen, all that is required is that the chosen beam be sufficiently focused or concentrated such that beam radius is sufficiently less than the radius of hole 14. As beam 16 enters through hole 14, it strikes rotatable mirror 18 located at the first focal point of the ellipse. Depending upon the amount of rotation, the longitudinal axis of beam 16 forms a variable angle $\alpha$ with the longitudinal axis of rotatable mirror 18. Also, depending upon the amount of rotation of rotatable mirror 18, reflecting beam 20 will strike elliptical mirror 12 at varying locations upon mirror 12. Thus, a steeper incline of rotatable mirror 18, or larger angle $\alpha$, will cause reflecting beam 20 to strike elliptical mirror 12 nearer hole 14. Conversely, a shallower incline will cause reflecting beam 20 to strike elliptical mirror 12 at a point further from hole 14.

In keeping with the invention, it is important to note that a sealing member 21 such as a beam-transmissive window can be substituted for, or placed in, hole 14. The sealing member 21 functions to allow beam 16 to enter a vacuum sealed chamber defined by elliptical mirror 12 and another sealing member 23 at the open end of elliptical mirror 12. A vacuum sealed chamber is preferred in instances where rotatable mirror 18 and reflecting beam 20 need be acclimated to a vacuum environment. However, in carrying out the invention, it is not necessary that reflecting beam 20 operate in a vacuum environment. In particular, it is not necessary that there even be a hole or that there is a full elliptical mirror. In other words, all that is necessary is that a segment of an elliptical mirror be placed so as to generate first and second focal points at the surface of rotatable mirror 18 and target 22. This can be achieved by passing beam 16 adjacent to one end of an elliptical mirror segment, wherein the segment is suspended at a location necessary to receive and generate reflected beams at focal points similar to the non-segmented or "full" elliptical mirror 12.

One of the important features of variable angle, fixed position device 10 is where elliptical mirror 12 causes reflecting beam 20 to strike target 22 at a fixed point located at the second focal point of the ellipse regardless of where reflecting beam 20 strikes elliptical mirror 12. Consequently, the fixed point of incidence upon target 22 is not effected by the rotation of rotatable mirror 18. Also, another important feature of variable angle, fixed position device 10 is that the travel path length of reflected beam 20 from rotatable mirror 18 to target 22 is constant regardless of the changes in angle $\alpha$ of rotatable mirror 18. Since the path length of reflecting beam 20 is constant, the travel time, T, of reflected beam 20 is also constant and can be expressed in the following formula:

$$T_f = \frac{1}{c}[3a - \sqrt{a^2 - b^2}]$$

where a and b are respectively, the major and minor axes of the ellipse and c is the speed of light. Although both travel time and point of incidence upon target 22 are constant regardless of changes in $\alpha$, angle of incidence ($\phi$) will change in accordance with changes in $\alpha$. Variable angle, fixed position device 10 requires that angle of incidence, $\phi$, be variable in accordance with the variability in angle $\alpha$. In general, the angle of incidence, $\phi$ at target 22 is given in terms of the rotatable mirror angle, $\alpha$, by the following formula:

$$\phi = \sin^{-1}\left[\frac{b^2\sin(2\alpha)}{2a^2 - b^2 - 2a\sqrt{a^2 - b^2}\cos(2\alpha)}\right]$$

It is important to note that, depending upon the magnitude of a and b, approximately a 2:1 gearing ratio between $\alpha$ and $\phi$ exists. This is a desirable outcome since it provides controllability with a high degree of precision in changes of $\phi$ relative to larger changes in $\alpha$.

There are numerous changes that can be made to variable angle, fixed position device 10 without substantially changing the function of the device. For example, rotatable mirror 18 can be either curved or flat depending upon the characteristics of elliptical mirror 12. If elliptical mirror 12 is a true ellipsoid (three dimensional elliptical pattern formed by rotatable an ellipse around either axis), then the reflecting surface of rotatable mirror 18 can be flat. If, however, elliptical mirror 12 is not an ellipsoid but is an elliptically curved mirror which extends directly upward in the Z direction in accordance with the XY ellipse pattern, then the reflecting surface of rotatable mirror 18 can be curved, wherein the curvature is used to compensate for partial astigmatic corrections that must be made. Further, curvature of the rotatable mirror can provide additional focussing or defocussing depending on the specific application. The rotatable mirror may also be a phase conjugate mirror in order to correct for phase front distortion. Alternatively, a small, collimated rotatable light source, such as a semiconductor diode laser, may replace the rotatable mirror. In addition to rotatable mirror 18 being either flat or curved, mirror 18 can be easily controlled by mechanical or electrical actuators which function to rotate mirror 18 in a controllable, pre-defined pattern. Pursuant to movement of mirror 18, it is noted that mirror 18 can be rotated either continuously or in discrete movements whereby beam 16 impinges upon mirror 18 either during the continuous rotatable movement or between discrete movements. Although continuous rotatable movement will carry out the invention, it is sometimes preferable that mirror 18 be rotatable in discrete movements with beam 16 striking the surface of mirror 18 between each movement.

Figure 2:
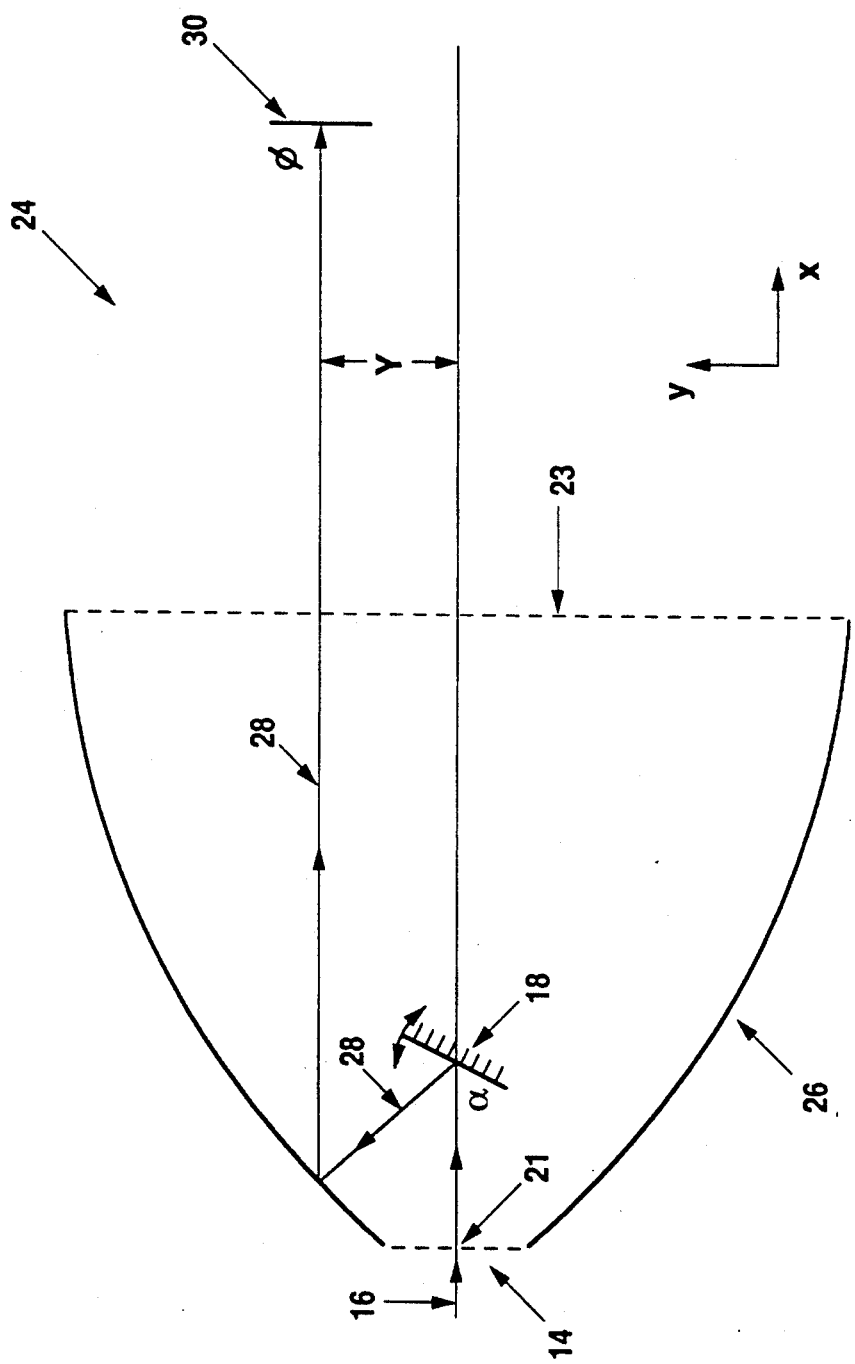
FIG. 2 is a cross-sectional view of a variable position, fixed angle beam alignment device of the present invention.

FIG. 2 illustrates another embodiment of the present invention showing the variable position, fixed angle beam alignment device 24 having a parabolic mirror 26. Parabolic mirror 26 functions to receive optical beam 16, aligned along the axis of the parabola, through a hole 14 within parabolic mirror 26. Upon striking rotatable mirror 18, located at the focus of the parabola, optical beam 16 is reflected as reflecting beam 28. Reflecting beam 28 then strikes parabolic mirror 26 to be reflected back at an angle parallel to the X-axis of parabolic mirror 26.

An important feature of variable position, fixed angle device 24 is that reflecting beam 28 strikes a target 30 at various locations depending upon the amount of rotation or changes in $\alpha$ of rotatable mirror 18. Although the point of incidence upon target 30 is variable, reflecting beam 28 will strike target 30 at a fixed angle of incidence, $\phi$, regardless of the changes in angle $\alpha$. Reflecting beam 28 will maintain a path parallel to the optical beam 16 path and will be displaced a distance Y away from the path of beam 16 according to the following formula:

$$Y = \frac{1 - \sin(\alpha)}{2d\cos(\alpha)}$$

where $x = dy^2$, defines the parabola.

In accordance with variable position, fixed angle device 24, the travel distance of reflecting beam 28 remains constant regardless of the changes in $\alpha$, as long as $\phi = 90$ degrees. Since the travel distance is constant, so must be the travel time of reflecting beam 28 as it travels between rotatable mirror 18 and target 30. Like the elliptical embodiment, the parabolic embodiment of variable position, fixed angle device 24 provides synchronized arrival of optical beams upon target 30. The time of flight through variable position, fixed angle device 24 can be described by the following formula:

$$T_f = \frac{1}{c}\left[\frac{1 + 4dX_s}{4d}\right]$$

where target 30 is situated upon the plane $x = X_s$.

Similar to variable angle, fixed position device 10, variable position, fixed angle device 24 can include either a flat or a curved reflecting surface of rotatable mirror 18 depending upon whether or not parabolic mirror 26 is a paraboloid. If mirror 26 is not a paraboloid but is merely a parabola extending directly upward into the Z-axis, then a curved surface on rotatable mirror may be desired to correct for the astigmatic surface of the Z-extending parabola. Conversely, if mirror 26 is a paraboloid, then the surface of rotatable mirror 18 may be flat. The curvature of the rotatable mirror can also provide additional focussing or defocussing, depending on the given application. The rotatable mirror may also be a phase conjugate mirror in order to correct for phase front distortion. Alternatively, a small, collimated rotatable light source, such as a semiconductor diode laser, may replace the rotatable mirror.

In keeping with the invention, it is important to note that, like the elliptical mirror embodiment, parabolic mirror 26 can utilize a sealing member or window 21 placed in hole 14. The sealing member 21 can provide a vacuum sealed chamber through which reflected beam 28 travels. Also, a partial parabolic mirror or segment absent hole 14 can be used instead of a full parabolic mirror having hole 14 through which beam 16 travels.

Figure 3:
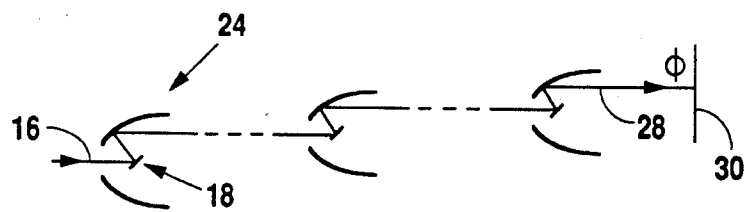
FIG. 3 is a cross-sectional view of cascaded variable position, fixed angle beam alignment devices of the present invention.

It is important to note that variable angle, fixed position device 10 and variable position, fixed angle device 24 can be used as building blocks and can be cascaded together in any combination sufficient to provide flexible steering for any beam alignment task. As illustrated in FIG. 3, a plurality of fixed angle devices 24 are shown cascaded together. The cascaded arrangement of fixed angle devices 24 provides a reflecting beam 28 which strikes target 30 at a fixed angle φ regardless of the amount of rotation of each mirror 18. The rotatable mirrors 18 can be simultaneously rotated or rotated independently of one another depending upon where the designer wants to steer the reflecting beam upon target 30. Also, the amount of rotation can be adjusted so as to align beams 16 and 28 of each fixed angle device 24 with beams 16 and 28 of proceeding and subsequent fixed angle devices 24. It is important to note that design advantages are gained even if only one mirror is rotatable. If necessary, the downstream devices may be translated perpendicular to the direction of propagation for improved alignment.

Figure 4:
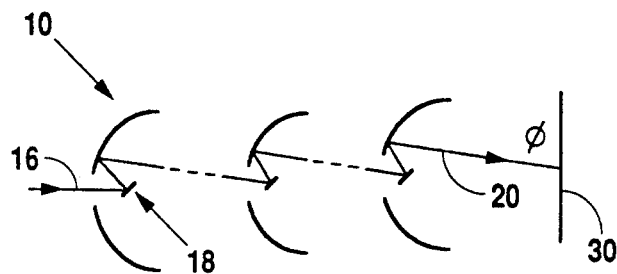
FIG. 4 is a cross-sectional view of cascaded variable angle, fixed position beam alignment devices of the present invention.

FIG. 4 illustrates a cascaded arrangement of variable angle, fixed position devices 10, wherein reflecting beam 20 is placed at a fixed point upon target 30 in response to movement of rotatable mirrors 18. Again, rotatable mirrors 18 can be moved simultaneously or independently of each other depending upon alignment constraints between each fixed position device and the desired position upon target 30. If necessary the downstream devices may be rotated about the axis of propagation for improved alignment. As illustrated, the cascaded ellipses must share common focal points.

Figure 5:
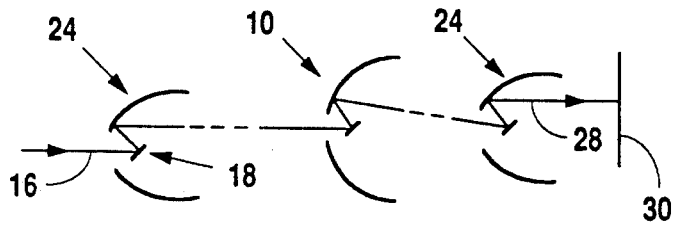
FIG. 5 is a cross-sectional view of a combination of cascaded variable angle, fixed position beam alignment devices and variable position, fixed angle beam alignment devices of the present invention.

FIG. 5 illustrates a combination of variable angle, fixed position devices 10 and variable position, fixed angle devices 24 that can be arranged in any cascaded format depending upon the desired beam alignment task. FIG. 5 shows variable position, fixed angle device 24 receiving optical beam 16 and a subsequent variable position, fixed angle device 24 delivering reflecting beam 28 upon target 30. If necessary, the downstream devices may be translated or rotated for improved alignment. It is important to note, however, that variable angle, fixed position devices 10 can be substituted for variable position, fixed angle devices 24 without deviating from the scope of the invention. The arrangement of the devices 10 and 24 as building blocks in the beam alignment scheme can be varied for any outcome desired by the optical designer.

Figure 6:
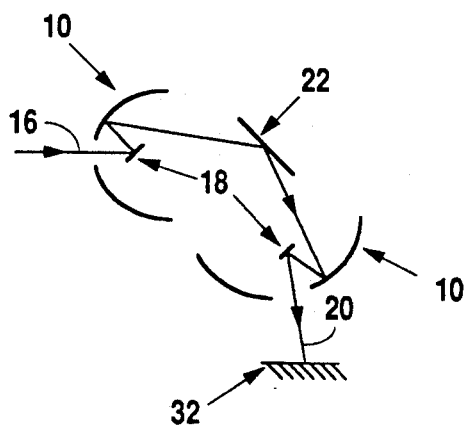
FIG. 6 is a cross-sectional view of two variable angle, fixed position beam alignment devices of the present invention connected in tandem.

FIG. 6 illustrates that fixed position devices 10 can be arranged in tandem to realign optical beam 16 into reflecting beam 20. Instead of reflecting beam 20 being transmitted away from hole 14 and towards a target, it can be transmitted back towards and through hole 14 and away from target 22 as shown. The tandem arrangement of FIG. 6 can be used in multi-spectral angular scanning applications. Multi-spectral angular scanning is useful in ellipsometry, thin film characterization and industrial vision system applications. In the tandem configuration, target 22 is placed at the common focus of two ellipses as shown. Optical beam 16 is projected through hole 14 of one variable angle, fixed position device 10 and then imaged onto target 22. The beam reflected off target 22 is then collected and directed onto a detector 32 by the second variable angle, fixed position device 10. The two rotatable mirrors 18 can move in concert either through an appropriate mechanical linkage or through computer controlled actuators, in order to provide variable and differential angle scanning. In this manner, optical beam 16, target 22 and detector 32 may be fixed in place during the scan. This is useful for two reasons. Typically, the optical source which provides optical beam 16 and the detector 32 may be large and bulky assemblies, and precise relative movement of these assemblies are not needed if mirrors 18 are moved instead. Thus, mirror movement compensates for lack in movement of the assemblies. Also, there is an additional degree of freedom associated with target 22, and thus, it may be irradiated by an extremely aligned pump laser or particle beam, or mounted on a traditional conveyor belt.

Figure 7:
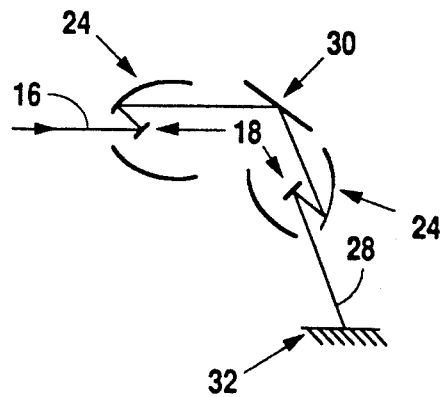
FIG. 7 is a cross-sectional view of two variable position, fixed angle beam alignment devices of the present invention connected in tandem.

FIG. 7 illustrates that variable position, fixed angle devices 24 can also be arranged in tandem similar to the variable angle, fixed position devices 10 of FIG. 6. Tandem arrangement will provide the same advantages previously described. However, using variable position, fixed angle devices 24 will provide an additional degree of freedom in aligning reflecting beam 28 upon detector 32. Depending upon the relative location of incoming optical beam 16 and outgoing reflecting beam 28, tandemly arranged variable position, fixed angle devices 24 might be preferred to tandemly arranged variable angle, fixed position devices 10.

Figure 8:
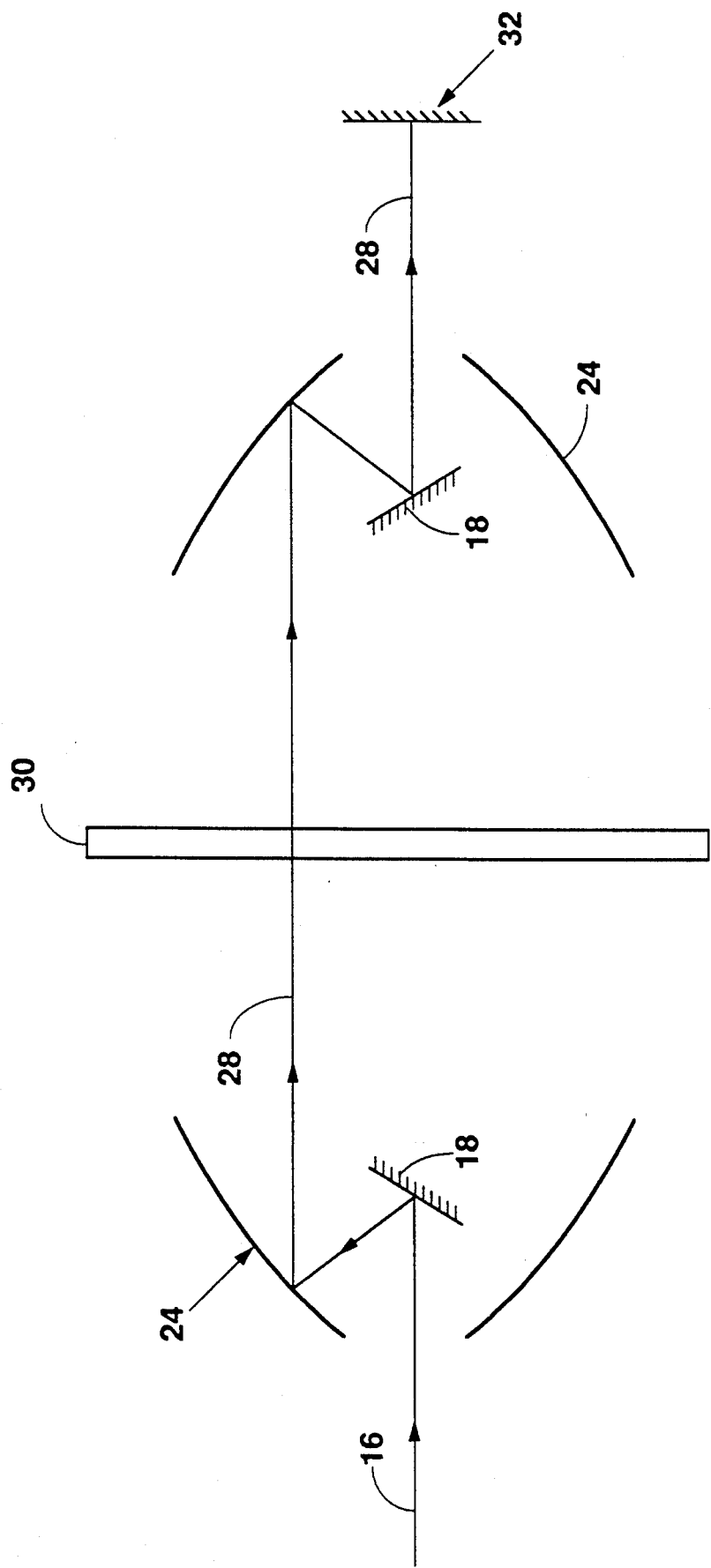
FIG. 8 is a cross-sectional view of two variable position, fixed angle devices of the present invention used in tandem to measure the transmission through a target as a function of position.
Figure 9:
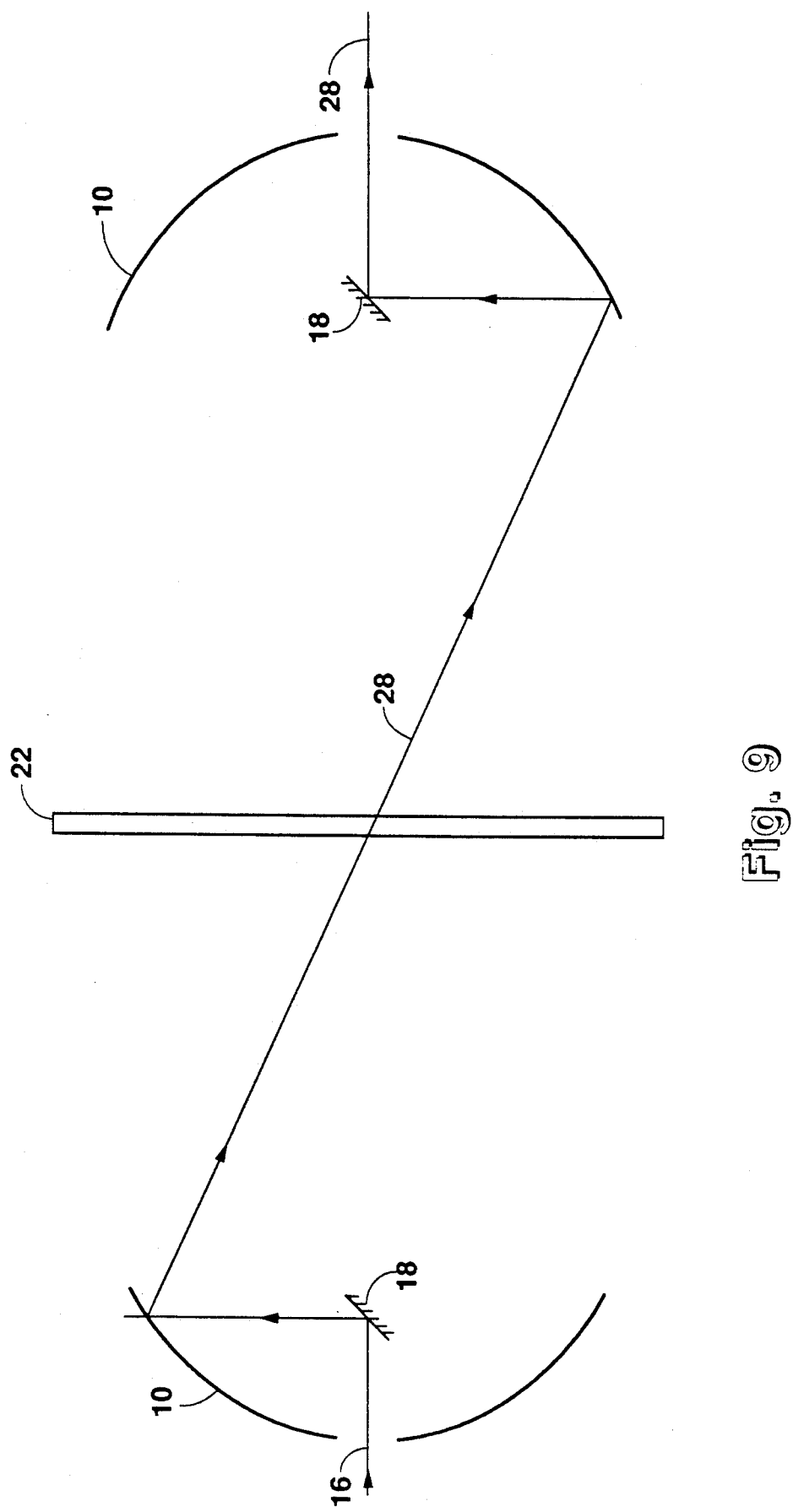
FIG. 9 is a cross-sectional view of two variable angle, fixed position devices of the present invention used in tandem to measure the transmission through a target as a function of angle.

FIG. 8 illustrates that two variable position, fixed angle devices 24 can also be arranged in tandem to measure the transmission through target 30 as a function of position, or, more generally, to vary the optical properties of reflecting beam 28 by a target 30 whose transmission properties may purposefully vary as a function of position. The first variable position, fixed angle device 24 adjusts the position of incidence upon target 30. The second variable position, fixed angle device 24 can, for example, redirect the beam back along the original path of propagation and into a fixed detector 32. FIG. 9 illustrates that two variable angle, fixed position devices 10 that can also be arranged in tandem to measure the transmission through target 22 as a function of angle, or, more generally, to vary the optical properties of the beam by target 22 whose transmission properties purposefully vary as a function of angle of incidence. The first variable angle, fixed position device 10 adjusts the angle of incidence upon target 22. The second variable angle, fixed position device 10, can, for example, redirect the beam back along the original path of propagation, into a fixed detector. The second focal point of each ellipse is common and defines the location of target 22.

The foregoing description of the invention has been directed to multiple preferred embodiments of the present invention. It will be apparent, however, to those skilled in the art that modifications and changes in both apparatus and method may be made without departing from the scope and spirit of the invention. For example, instead of using elliptical and parabolic mirrors, ellipsoid and paraboloid mirrors can be used. Also, either flat or curved surfaces can be used upon rotatable mirror 18. Also, the physical size of these devices are scalable from the micron size for photonic applications to the meter size for astronomical and industrial applications. Also, as shown in FIGS. 3-8, variable angle, fixed position devices 10 and variable position, fixed angle devices 24 can be arranged in cascaded or tandem fashion to achieve any desired beam alignment outcome. Also, it is appreciated by one skilled in the art that the precision by which reflected beams are placed upon target is dependent upon smoothness or surface quality of mirrors 12, 18 and/or 26. If the mirrors are of high optical quality, then placement of reflected beam 20 or angle of incidence of reflected beam 28 will not deviate substantially during the rotation of mirror 18. High quality mirrors presently exist which can fix the amount of deviation to be less than 10%, and in some instances, less than 1%. Therefore, it is the applicants' intention in the following claims to cover all such equivalent modifications and variations which fall within the true spirit and scope of the invention.

What is claimed is:

1. A device for aligning optical beams, comprising:
an elliptical mirror having an axis, said elliptical mirror having a first end and a second end, said first end including an aperture with a central axis linearly aligned with the foci of said elliptical mirror, wherein said first end and said second end include sealing means for providing a vacuum sealed chamber;
a rotatable mirror aligned with said axis for reflecting optical beams traveling along said axis to said elliptical mirror, said rotatable mirror being configured at a first focal point of said elliptical mirror; and
a target for receiving reflected beams from said elliptical mirror, whereby each of said reflected beams from said rotatable mirror travel a predetermine distance to the target dependence of an angle of rotation of said rotatable mirror, said target being configured a second focal point of said elliptical mirror.

2. A device for aligning optical beams, comprising:
an elliptical mirror having an axis, said elliptical mirror having a first end and a second end, said first end including an aperture with a central axis linearly aligned with the foci of said elliptical mirror, wherein said first end and said second end include sealing means for providing a vacuum sealed chamber;
a rotatable mirror aligned with said axis for reflecting optical beams traveling along said axis to said elliptical mirror, said rotatable mirror having a curved surface upon which said optical beams are reflected; and
a target for receiving reflected beams from said elliptical mirror, whereby each of said reflected beams from said rotatable mirror travel a predetermined distance to the target independent of an angle of rotation of said rotatable mirror.

3. A device for aligning optical beams, comprising:
an elliptical mirror having an axis, said elliptical mirror having a first end and a second end, said first end including an aperture with a central axis linearly aligned with the foci of said elliptical mirror, wherein said first end and said second end include sealing means for providing a vacuum sealed chamber; said elliptical mirror being a two dimensional ellipse extending directly upward to form a three dimensional elliptically curved mirror;
a rotatable mirror aligned with said axis for reflecting optical beams traveling along said axis to said elliptical mirror; and
a target for receiving reflected beams from said elliptical mirror, whereby each of said reflected beams from said rotatable mirror travel a predetermined distance to the target independent of an angle of rotation of said rotatable mirror.

4. A device for aligning optical beams, comprising:
an elliptical mirror having an axis, said elliptical mirror having a first end and a second end, said first end including an aperture with a central axis linearly aligned with the foci of said elliptical mirror, wherein said first end and said second end include sealing means for providing a vacuum sealed chamber, said elliptical mirror being a three dimensional ellipsoid;
a rotatable mirror aligned with said axis for reflecting optical beams traveling along said axis to said elliptical mirror; and
a target for receiving reflected beams from said elliptical mirror, whereby each of said reflected beams from said rotatable mirror travel a predetermined distance to the target independent of an angle of rotation of said rotatable mirror.

5. A cascading beam alignment device used for steering and aligning an optical beam, said beam alignment device comprising:
(a) a first elliptical mirror having first and second foci;
(b) a second elliptical mirror having third and fourth foci, wherein the second focus and the third focus coincide;
(c) a first rotatable mirror mounted at the first focus of the first elliptical mirror;
(d) a second rotatable mirror mounted at the third focus of the second elliptical mirror; and
(d) a target mounted at the fourth focus of the second elliptical mirror.

6. The cascading beam alignment device of claim 5 wherein either the first or the second elliptical mirror comprises a two dimensional ellipse extending directly upward to form a three dimensional elliptically curved mirror.

7. The cascading beam alignment device of claim 5 wherein either the first or the second elliptical mirror is a three dimensional ellipsoid.

8. The cascading beam alignment device of claim 5, wherein either the first or the second rotatable mirror includes a reflecting surface adapted to rotate about a central axis, said central axis being aligned perpendicular to a beam path of impinging optical beams.

9. The cascading beam alignment device of claim 5 wherein either the first or the second rotatable mirror comprises a cured surface upon which optical beams are reflected.

10. The cascading beam alignment device of claim 5 wherein either the first or the second rotatable mirror comprise a flat surface form which optical beams are reflected.

* * * * *

UNITED STATES PATENT AND TRADEMARK OFFICE
CERTIFICATE OF CORRECTION

PATENT NO. : 5,307,210
DATED : April 26, 1994
INVENTOR(S) : MacFarlane, et al

It is certified that error appears in the above-indentified patent and that said Letters Patent is hereby corrected as shown below:

In claim 1, column 9, line 41, change "dependence" to --independent--.

In claim 8, column 10, line 54, change "5," to --5--.

In claim 9, column 10, line 61, change "cured" to --curved--.

In claim 10, column 10, line 65, change "comprise" to --comprises--.

In claim 10, column 10, line 65, change "form" to --from--.

Signed and Sealed this

Sixteenth Day of August, 1994

Attest:

BRUCE LEHMAN

Attesting Officer     Commissioner of Patents and Trademarks